United States Patent
Yang

Patent Number: 5,623,255
Date of Patent: Apr. 22, 1997

[54] TESTING WRISTLET SEAT

[76] Inventor: Shin-Ming Yang, 3F., No. 15, Sec. 4, Shing-Long Rd., Taipei, Taiwan

[21] Appl. No.: 600,778

[22] Filed: Feb. 13, 1996

[30] Foreign Application Priority Data

Mar. 10, 1995 [CN] China .............. 95 2 04173.1

[51] Int. Cl.⁶ ............................................. G08B 21/00
[52] U.S. Cl. .................. 340/649; 340/650; 340/657; 361/212; 361/220
[58] Field of Search ............................ 340/649, 650, 340/657, 658; 324/509, 510; 361/220, 212

[56] References Cited

U.S. PATENT DOCUMENTS

| | | | |
|---|---|---|---|
| 4,605,984 | 8/1986 | Fiedler | 361/220 |
| 4,638,399 | 1/1987 | Maroney et al. | 340/649 |
| 4,639,825 | 1/1987 | Breidegam | 361/212 |
| 4,813,459 | 3/1989 | Breidegam | 361/220 |
| 4,847,729 | 7/1989 | Hee | 361/220 |
| 5,218,306 | 6/1993 | Bakhoum | 340/649 |
| 5,408,186 | 4/1995 | Bakhoum | 340/649 |
| 5,457,596 | 10/1995 | Yang | 361/220 |
| 5,463,379 | 10/1995 | Campbell et al. | 340/649 |
| 5,519,384 | 5/1996 | Chanudet et al. | 340/649 |

Primary Examiner—Brent A. Swarthout
Assistant Examiner—Van T. Trieu
Attorney, Agent, or Firm—Keith Kline

[57] ABSTRACT

A testing wristlet seat using an oscillation circuit to test a test lead which is grounded to discharge the static electricity produced in the manufacturing procedure. In case the test lead is broken or poorly grounded, the grounding condition will no more exist. At this time, the oscillation circuit oscillates and generates a frequency to make an inner buzzer emit warning sound to inform the user of the breakage of the circuit. An LCD display screen is disposed on the wristlet seat for displaying time in normal condition. In case a failure takes place, the display screen displays a fail signal for the user.

2 Claims, 6 Drawing Sheets

TESTING WRISTLET SEAT

BACKGROUND OF THE INVENTION

The present invention relates to a testing wristlet seat, and more particularly to a testing wristlet seat for testing the static grounding condition. The testing wristlet seat is provided with a display screen for displaying time in normal condition. In case a failure of grounding takes place, the wristlet seat emits a warning sound and the display screen displays a fail signal for the user.

Nowadays, more and more electronic products are manufactured of chips. This is especially true for the high technical products such as communication equipments, computers, etc. The so-called chip means a circuit in which all the electronic parts are burned so as to simplify the circuit and minimize the volume thereof for achieving a large size integrated circuit (LSI) or very large size integrated circuit (VLSI). With the existing technology, the chip can be manufactured as complementary-symmetry metal oxide semiconductor, that is, CMOS electronic element. Such CMOS electronic element is extremely apt to be damaged by static electricity.

During the manufacturing procedure, in case the manufacturer fails to provide a staticproof measure for the CMOS element, the defect ratio of the product will be inevitably greatly increased and thus the product will have low stability and high manufacturing cost. Therefore, during the entire manufacturing procedure, the issue of static-protection should be highly appreciated.

FIG. 1 shows a conventional static wristlet seat 1 having an extending test lead 2 for connecting the wristlet seat 1 with a test instrument 3 to form a circuit. The wristlet seat 1 serves to conduct the static electricity of human body through the circuit for testing whether the test lead 2 is broken. Because the test instrument 3 does not provide a grounding condition, the static electricity cannot be removed. Moreover, for testing whether the test lead 2 is broken, with respect to the manufacturer, when actually used, only the test lead 2 is grounded without the test instrument 3. At this time, it can be no more tested whether the test lead 2 is broken.

FIG. 2 shows another conventional static wristlet seat 4 improved from the above wristlet seat 1, in which the circuit inside the test instrument 3 is minimized and installed in the wristlet seat 4. Accordingly, the test button 31 of the circuit is changed into active test. This is not really applicable by reasons as follows:

1. In case the test lead 2 is connected in the same manner as the preceding conventional wristlet seat 1, then one end of the test lead 2 must be inserted into the wristlet seat 4 and the other end of the test lead 2 should contact with the bottom conductive board of the wristlet seat 4 to form a circuit. Therefore, only it is tested whether the test lead 2 is broken, while the static electricity cannot be removed to the ground.

2. In case the test lead 2 is connected to the ground, then the wristlet seat 4, test lead 2, the ground and human body together form a one-way straight line rather than a circuit. Therefore, only the static electricity is removed, while it cannot be tested whether the test lead 2 is broken.

Moreover, it is unsuitable for a general operator to wear the wristlet seat 1 and a watch when working in the operation area. This is because that the watch is conductive and will incur second static discharge. Therefore, the operator can hardly fully control the operation time. However, this problem can be solved by adding time display function to the wristlet seat.

SUMMARY OF THE INVENTION

It is therefore a primary object of the present invention to provide a testing wristlet seat which is able to test whether the grounding lead is broken and display state and time. The grounding lead of the wristlet seat forms a circuit for testing whether the grounding wire and the test wire form a complete circuit.

The present invention can be best understood through the following description and accompanying drawing, wherein:

DETAILED DESCRIPTION OF THE PREFERRED EMBODIMENT

Figure 1:
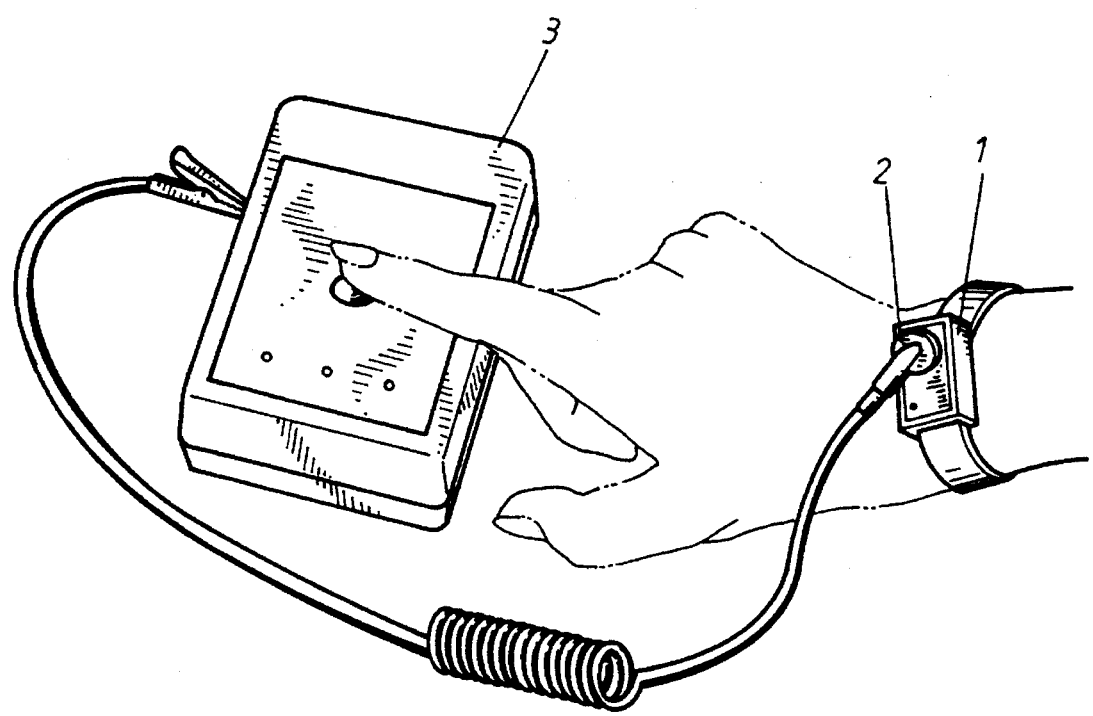
FIG. 1 shows the operation of a conventional staticproof wristlet seat and cooperative test instrument.
Figure 2:
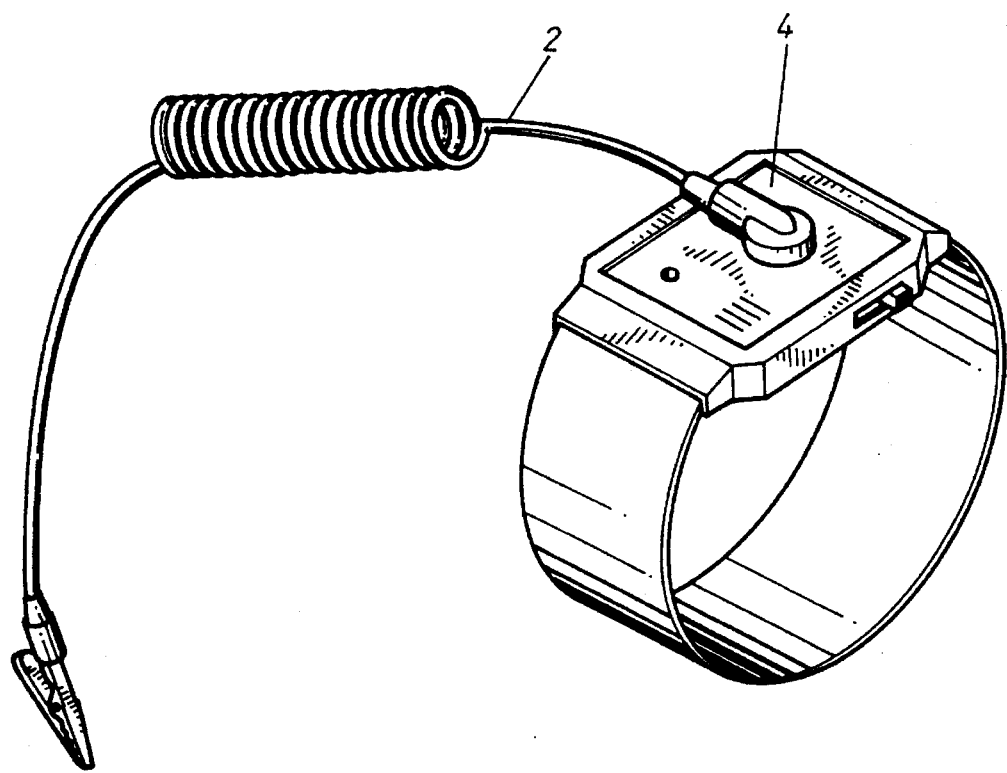
FIG. 2 is a perspective view of another conventional testing wristlet seat.
Figure 3:
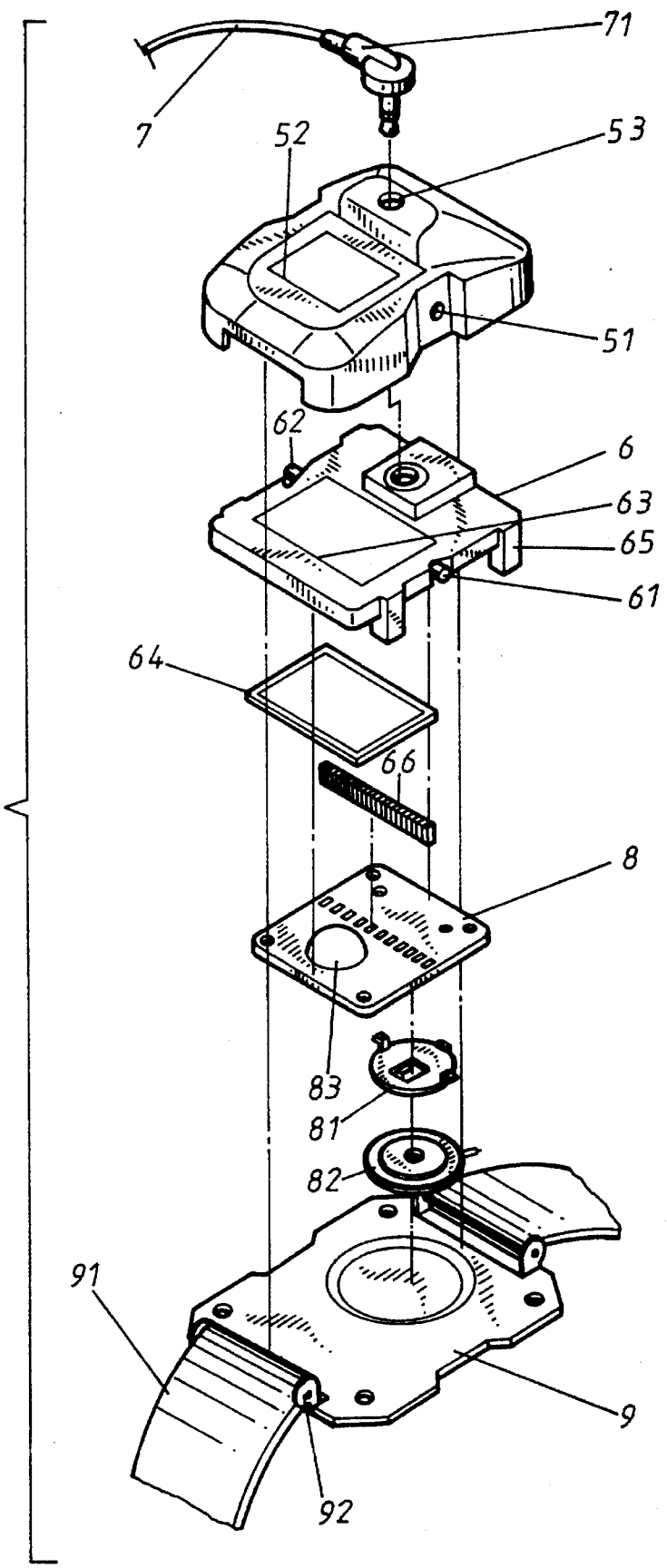
FIG. 3 is a perspective exploded view of the testing wristlet seat of the present invention.
Figure 4:
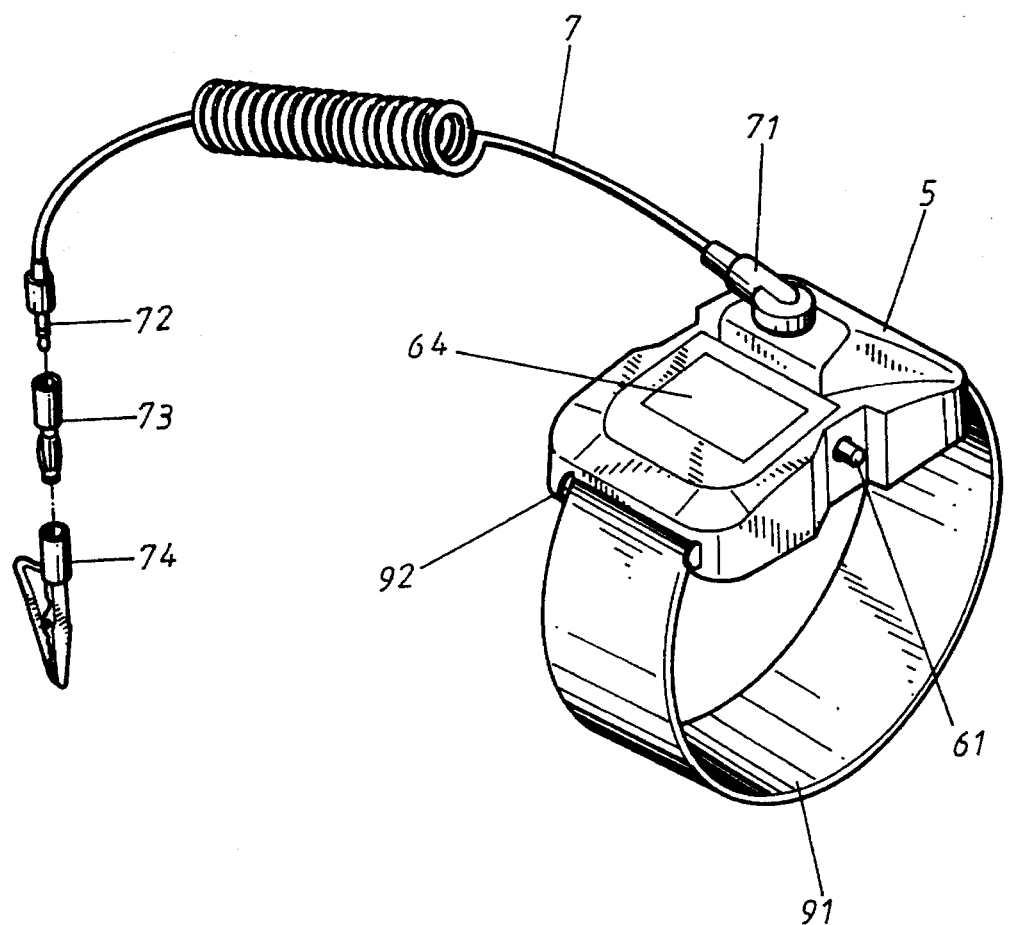
FIG. 4 is a perspective assembled view of the testing wristlet seat of the present invention.

Please refer to FIGS. 3 and 4. The testing wristlet seat of the present invention includes a top cover 5 made of staticproof material and a wristlet core 6 disposed under the top cover 5. The top cover 5 is formed with two recesses on two lateral sides and two button holes 51 are disposed in the recesses. A display screen frame 52 is disposed on a front portion of the top cover 5. A convex is formed on a rear portion of the top cover 5 and a lead insertion hole 53 is formed on the convex.

The wristlet core 6 has the same profile as the top cover 5 and is located in the top cover 5. The wristlet core 6 is formed with two recesses on two lateral sides and two time-adjusting buttons 61, 62 are disposed in the recesses for setting time. The buttons 61, 62 are inserted in the button holes 51 of the top cover 5. A display screen frame 63 is disposed on a front portion of the wristlet core 6 for installing an LCD display screen 64 therein. After installed, the display screen 64 is further placed in the display screen frame 52 of the top cover 5. Several screw locking columns 65 are disposed under a bottom of the wristlet core 6. The grounding lead 7 has a first plug 71 at one end for inserting into the lead insertion hole 53 of the top cover 5, and a second plug 72 at the other end for connecting with a banana plug 73. The banana plug 73 connects with an alligator clip 74 which is optionally used according to the pattern of the grounding socket. The grounding lead 7 forms a double wire circuit for connecting to the ground or public grounding system.

The display screen 64 inserted in the display screen frame 63 of the wristlet core 6 is used to display time and output signal responsive to breakage of the wire or poor grounding. A conductive rubber 66 is disposed under the display screen 64 and contacts with the front face of a circuit board 8 for receiving the output signal from the circuit board 8. A cell latch member 81 is secured to the back face of the circuit board 8 by screws for placing a cell thereon. A buzzer 82 is disposed under the cell latch member 81, whereby when breakage of the wire or poor grounding takes place, the buzzer 82 emits a warning sound to alert the user for proper reaction. A conductive board 9 is located right under the buzzer 82 and contacts with the skin of the user for conducting the static electricity thereon toward the grounding lead 7 to be discharged to the public grounding system or the ground. Two pairs of pivot lugs 92 are disposed respectively on a front and a rear edges of the conductive board 9 for pivotally connecting with a wristlet belt 91 for wearing. Each screw locking column 65 of the wristlet core 6 is formed with a thread hole in which a screw is screwed to lock the circuit board 8 in the wristlet core 6 which is in turn placed into the top cover 5. Then the buzzer 82 and the conductive board 9 are installed into the top cover 5. The top cover 5 and the conductive board 9 are equipped with four corresponding screws so as to integrally associate together to form an assembly. The assembly with the pivotally connected wristlet belt 91 is shown in FIG. 4.

Figure 5:
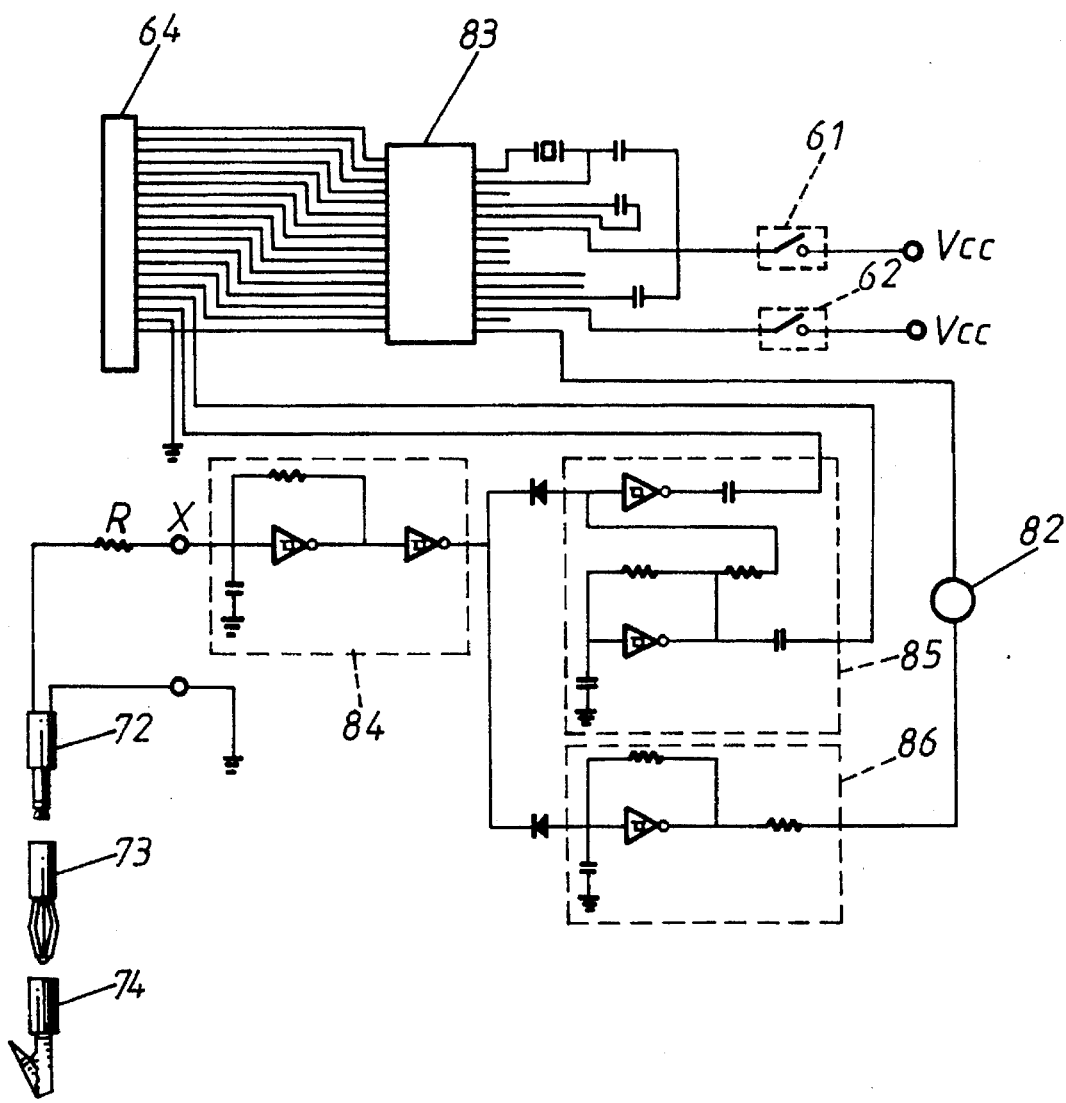
FIG. 5 is a circuit diagram of the testing circuit of the testing wristlet seat of the present invention.

FIG. 5 is a circuit diagram of the circuit of the present invention. The circuit is substantially divided into two parts to which two integrated circuits are responsive. A first integrated circuit 83 of the two integrated circuits is used to output the time and alarm. This integrated circuit 83 is connected to a crystal oscillator and multiple capacitors, serving as a time oscillation circuit. Two buttons 61, 62 are connected to the oscillation circuit for adjusting the time. Multiple output pins of the oscillation circuit are connected to the display screen 64 for displaying the time.

A second integrated circuit of the two integrated circuits is an oscillation integrated circuit. (In this embodiment, the oscillation integrated circuit is a Schmidt oscillation inverter.) The oscillation integrated circuit is used to output the respective necessary frequency of the device, such as the warning sound of the buzzer 82 and failure signal. According to the usage of the produced frequency, the oscillation circuit can be divided into basic frequency oscillator 84 for producing the necessary frequency for the respective oscillation circuits, fail oscillator 85 for producing two different frequencies, making the display screen generate a fail picture, and alarm oscillator 86 for producing a high frequency signal, making the buzzer 82 emit the warning sound.

The input terminal X of the circuit serves as the input terminal of the basic frequency oscillator 84 and connects with the lead insertion hole 53 of the top cover 5 and the conductive board 9, whereby after the plug 71 of the grounding lead 7 is inserted into the insertion hole, the static electricity generated by human body is conducted through a resistor R (which is a high impedance resistor for protecting human body from electric shock) to the alligator clip 74 of the grounding lead 7. The alligator clip 74 is connected to the ground to form a circuit.

When normally used, the static electricity of human body is conducted through the conductive board 9, lead insertion hole 53, plug 71 of the grounding lead 7, alligator clip 74 of the grounding lead 7 to the public grounding system or the ground. At this time, the input terminal X is in a grounding state with the basic frequency oscillator 84 not energized and the present time can be displayed on the display screen 64.

However, when the operator incautiously pulls and breaks the grounding lead 7 or the lead 7 is poorly grounded, the grounding condition of the input terminal X no more exists and the static electricity of human body cannot be discharged to the ground. At this time, the basic frequency oscillator 84 generates an oscillation frequency reverse-phase output from a Schmidt oscillation inverter. The reverse-phase working period is taken and output into two paths one of which is for the fail oscillator 85 and the other of which is for the alarm oscillator 86. The two oscillators work simultaneously.

With respect to the fail oscillator 85, the output is also divided into two paths one of which is reverse-phase output from a Schmidt oscillation inverter to connect with one pin of the display screen 64 and the other of which is input into the Schmidt oscillation inverter in order to oscillate the output oscillation frequency from the basic frequency oscillator 84 into a higher frequency and connect the same to another pin of the display screen 64. These two output frequencies make the display screen 64 output a fail signal.

With respect to the alarm oscillator 86, the basic frequency signal is oscillated into a high frequency signal which is transmitted to one end of the buzzer 82. The other end of the buzzer 82 is connected to the integrated circuit 83. This frequency will make the buzzer 82 emit a warning sound and make the integrated circuit 83 cooperate with the output signal from the fail oscillator 85, enabling the operator to see and hear the fail signal and promptly react for correction so as to avoid damage of product and increment of the defect ratio.

Figure 6:
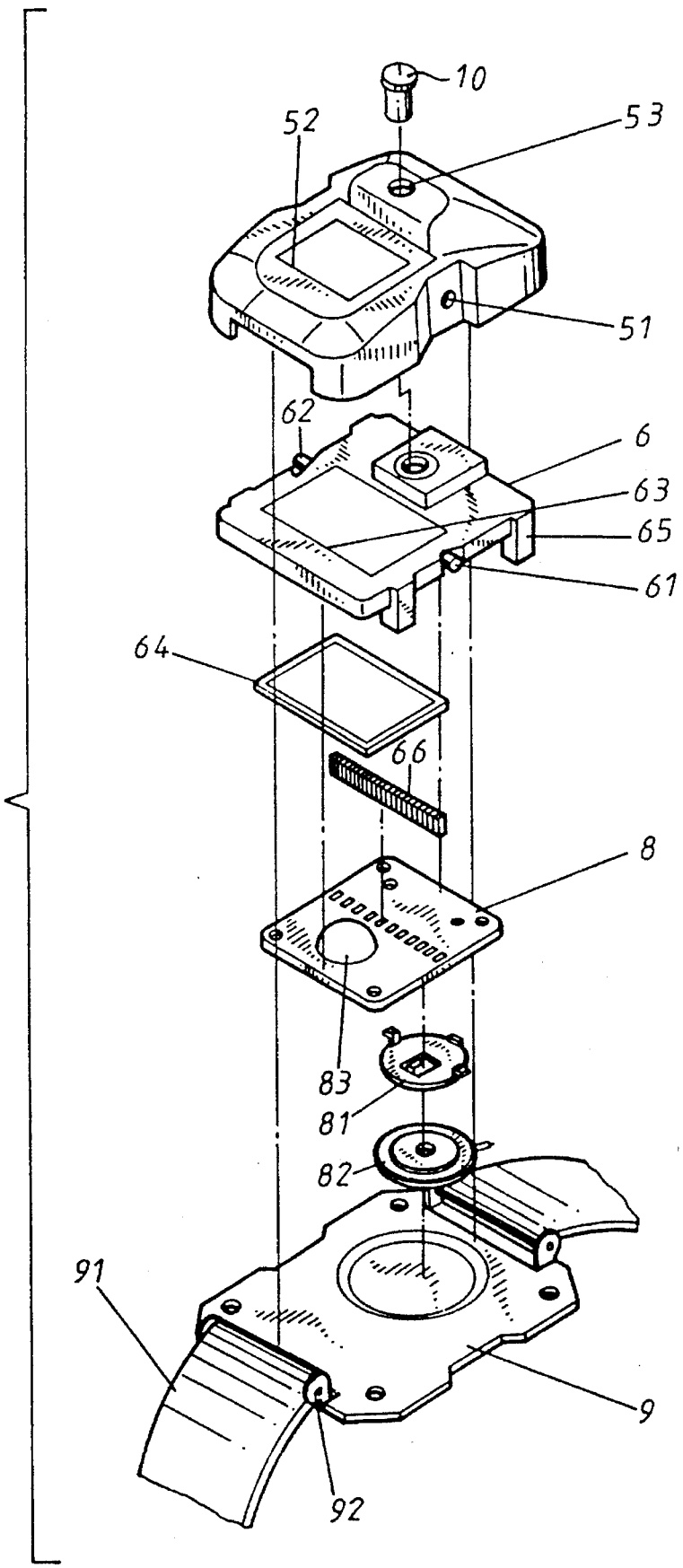
FIG. 6 is a perspective exploded view of the testing wristlet seat of the present invention in another aspect.

Please refer to FIG. 6. A conductive rubber 10 is inserted into the lead insertion hole 53 of the top cover 5 for displaying the time in normal condition.

According to the above arrangements, the present invention has the following advantages:

1. When normally used, the time is displayed, enabling the operator to control the time and work without wearing a watch. Therefore, the damage caused by the second static discharge is avoided.

2. The oscillation circuits can more precisely generate the respective necessary frequency for the device.

3. Two kinds of warning signals are generated simultaneously, so that the operator can perceive in time that the grounding condition no more exists and promptly react for correction.

4. The test instrument is combined in the wristlet seat to achieve a tidy appearance.

5. The banana plug is connected with the end of the grounding lead. When the banana plug is removed, the display screen will display the fail signal and a warning sound is emitted.

It is to be understood that the above description and drawings are only used for illustrating one embodiment of the present invention, not intended to limit the scope thereof. Any variation and derivation from the above description and drawings should be included in the scope of the present invention.

What is claimed is:

1. A testing wristlet seat comprising:

a top cover made of staticproof material and formed with two recesses on two lateral sides, two button holes being disposed in the recesses, a display screen frame being disposed on a front portion of the top cover, a convex lead insertion seat being formed on a rear portion of the top cover, a lead insertion hole being formed on the lead insertion seat;

a wristlet core located under the top cover and formed with two recesses on two lateral sides, two time-adjusting buttons being disposed in the recesses for setting time, the buttons being inserted in the button holes of the top cover, a display screen frame being disposed on a front portion of the wristlet core for installing a display screen therein, several screw locking columns being disposed under a bottom of the wristlet core;

a circuit board disposed in the top cover, a display screen being connected on a front face of the circuit board, the lead insertion seat of the top cover being electrically connected with the front face of the circuit board, a buzzer being connected on a back face of the circuit board, a controlling circuit being disposed in the circuit board for testing whether the static grounding lead is broken;

a conductive board serving as a bottom board of the top cover and contacting with human skin, the lead insertion seat of the top cover being electrically connected with the conductive board, pivot lugs being disposed respectively on a front and a rear edges of the conductive board for pivotally connecting with a wristlet belt for a user to wear the wristlet seat, the conductive board being formed with thread holes corresponding to the screw locking columns of the wristlet core; and a grounding lead having a first plug at one end for inserting into the lead insertion hole of the top cover, and a second plug at the other end for connecting with a banana plug which connects with an alligator clip, said wristlet seat being characterized in that the display screen and the circuit board are locked in the wristlet core by screws and the wristlet core is placed into the top cover and then the buzzer and the conductive board are installed into the top cover with wristlet belt pivotally connected to the conductive board, the alligator clip of the lead being connected to a public grounding system or the ground so that the controlling circuit and the public grounding system or the ground form a circuit for discharging the static electricity of human body to the ground and testing whether the lead is broken.

2. A testing wristlet seat as claimed in claim 1, wherein the controlling circuit comprises:

a first integrated circuit used to output the time and alarm, the first integrated circuit being connected to a crystal oscillator and multiple capacitors, the first integrated circuit serving as a time oscillation circuit, two buttons being connected to the oscillation circuit for adjusting the time, multiple output pins of the oscillation circuit being connected to the display screen for displaying the time;

a basic frequency oscillator which, when the grounding condition no longer exists and the static electricity of the human body cannot be discharged to the ground, produces an oscillation frequency to be output from an oscillation inverter;

a fail oscillator for producing two kinds of output frequencies, making the display screen output a picture; and an alarm oscillator for oscillating the basic frequency signal into a high frequency which makes the buzzer emit a warning sound, whereby when an operator pulls and breaks the grounding lead or the lead is poorly grounded, the basic frequency oscillator generates an oscillation frequency reverse-phase output by an oscillation inverter to the fail oscillator and the alarm oscillator, the two oscillators working simultaneously, and with respect to the fail oscillator, the output is divided into two paths one of which is a reverse-phase output from an oscillation inverter to connect with the display screen and the other of which is input into an oscillation circuit in order to oscillate the output oscillation frequency from the basic frequency oscillator into a higher frequency connected with the display screen, these two output frequencies making the display screen output a fail picture, and with respect to the alarm oscillator, the basic frequency signal is oscillated into a high frequency signal which is transmitted to one end of the buzzer, the other end of the buzzer being connected to the integrated circuit for time and alarm, this frequency making the buzzer emit a warning sound, enabling the operator to simultaneously see the fail picture and hear the buzzer promptly react.

* * * * *